(12) United States Patent
Cho-Chung (10) Patent No.: US 7,838,305 B2
(45) Date of Patent: Nov. 23, 2010

(54) AUTOANTIBODY DETECTION FOR CANCER DIAGNOSTICS

(75) Inventor: Yoon S. Cho-Chung, Bethesda, MD (US); Christina Chung, legal representative, Glendale, CA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 518 days.

(21) Appl. No.: 10/592,040

(22) PCT Filed: Mar. 7, 2005

(86) PCT No.: PCT/US2005/007203

§ 371 (c)(1),
(2), (4) Date: Oct. 23, 2007

(87) PCT Pub. No.: WO2005/088312

PCT Pub. Date: Sep. 22, 2005

(65) Prior Publication Data

US 2009/0123948 A1    May 14, 2009

Related U.S. Application Data

(60) Provisional application No. 60/550,348, filed on Mar. 8, 2004, provisional application No. 60/551,776, filed on Mar. 11, 2004.

(51) Int. Cl.
G01N 33/536 (2006.01)
(52) U.S. Cl. .................................................. 436/507
(58) Field of Classification Search .................. None
See application file for complete search history.

(56) References Cited

U.S. PATENT DOCUMENTS 7,402,403 B1 * 7/2008 Robertson et al. ............ 435/7.8

FOREIGN PATENT DOCUMENTS

| JP | 2002286716 A | 10/2002 |
|----|--------------|---------|
| JP | 2003503314 A | 1/2003 |
| WO | WO 00/78807 A1 | 12/2000 |
| WO | WO 00/79281 A1 | 12/2000 |

OTHER PUBLICATIONS

Amieux et al., *Ann. N.Y. Acad. Sci.*, 968, 75-95 (2002).
Cho et al., *Biochem. Bio. Res. Comm.*, 278 (3), 679-684 (2000).
Cho et al., *PNAS*, 97 (2), 835-840 (2000).
Cho-Chung et al., *Ann. N.Y. Acad. Sci.*, 968, 22-36 (2002).
Cho-Chung et al., *Cancer Inv.*, 7(2), 161-177 (1989).
Cho-Chung et al., *Crit. Rev. Oncol. Hematol.*, 21, 33-61 (1995).
Cho-Chung et al., *Front. Biosci.*, 4, D898-D907 (1999).
Cho-Chung et al., *Pharmac. Ther.*, 60, 265-288 (1993).
Cho-Chung, *Cancer Res.*, 50, 7093-7100 (1990).
Cho-Chung, *Cancer Treat. Res.*, 115, 123-143 (2003).
Cohen et al., *Anal. Biochem.*, 273, 89-97 (1999).
Eales, *Immunology for Life Scientists, Second Edition*, Ch. 5, 159-208 (2003).
Hong et al., *Chemistry Today*, 57-60 (2003).
Joos et al., *Electrophoresis*, 21, 2641-2650 (2000).
Kita et al., *Cancer Ltrs.*, 208, 187-191 (2004).
Krebs et al., *Ann. Rev. Biochem.*, 48, 923-959 (1979).
Lerner et al., *Leuk. Lymphoma*, 37 (1-2), 39-51 (2000).
Levy et al., *Mol. Endocrinol.*, 2(12), 1364-1373 (1988).
Matyakhina et al., *Ann. N.Y. Acac. Sci.*, 968, 148-157 (2002).
McKnight et al., *Recent Prog. Hormone Res.*, 44, 307-335 (1988).
Miller et al., *Eur. J. Cancer*, 29A(7), 989-991 (1993).
Tortora et al., *Ann. N.Y. Acad. Sci.*, 968, 139-147 (2002).
Aarts et al., *Cancer Research*, 62: 5770-5777 (2002).
Overwijk et al., *J. Exp. Med.*, 188(2): 277-286 (1998).
Disis et al., *Immunology*, 98: 192-199 1998).
Coggin Jr. et al. *Mod. Asp. Immunobiol.*, 16: 27-34 (2005).
Qiu et al., *Clin Lab Med* 29: 31-46 (2009).

* cited by examiner

*Primary Examiner*—Misook Yu
(74) *Attorney, Agent, or Firm*—Leydig, Voit & Mayer, Ltd.

(57) ABSTRACT

The present invention relates to compositions and methods for the detection of anti-ECPKA autoantibodies in a biological sample, and to the use of such compositions and methods in the diagnosis of cancer in humans and non-human mammals.

20 Claims, 7 Drawing Sheets

AUTOANTIBODY DETECTION FOR CANCER DIAGNOSTICS

CROSS-REFERENCE TO RELATED APPLICATIONS

This application claims a right of priority to U.S. Patent Application Ser. Nos. 60/550,348, filed Mar. 8, 2004, and 60/551,776 filed Mar. 11, 2004, which applications are hereby incorporated by reference in their entirety.

STATEMENT OF GOVERNMENTAL INTEREST

This invention was funded by NCI Intramural Research Program CCR at the National Institutes of Health. The United States Government has certain rights to this invention.

FIELD OF THE INVENTION

The present invention relates to compositions and methods for the detection of anti-ECPKA autoantibodies in a biological sample, and to the use of such compositions and methods in the diagnosis of cancer in humans and non-human mammals.

BACKGROUND OF THE INVENTION

Tumor markers are synthesized by malignant cells and released into the bloodstream. Such markers may also be produced by host tissues in response to invasion or as a result of tumor-induced metabolic changes. Tumor marker levels in blood or tissue fluids are helpful in diagnosing, screening, and monitoring tumor progression or regression. An ideal tumor marker would allow a simple blood test to detect cancer, and its levels would correlate with the stage of tumor progression. Due to the lack of sensitivity and specificity, however, no single marker has been previously established in a general healthy population or in most high-risk populations. The use of tumor markers in cancer diagnostics is well described (Sluss, P. M. et al [2004] "ESTABLISHMENT OF A CENTRAL LABORATORY SERUM TUMOR MARKER SERVICE ON A CONSOLIDATED IMMUNODIAGNOSTIC PLATFORM: DEVELOPMENT OF PRACTICE STANDARDS, SERVICE IMPROVEMENTS, AND OPERATIONAL EFFICIENCY," Clin Leadersh Manag Rev. 18 [1]:25-31; Gion, M. [2000] "SERUM TUMOUR MARKERS: FROM QUALITY CONTROL TO TOTAL QUALITY MANAGEMENT," Breast 9[6]:306-11; Wiesner, A. [2004] "DETECTION OF TUMOR MARKERS WITH PROTEINCHIP® TECHNOLOGY," Curr Pharm Biotechnol. February; 5[1]:45-67; Crawford, N. P. et al. [2003] "TUMOR MARKERS AND COLORECTAL CANCER: UTILITY IN MANAGEMENT," J Surg Oncol. 84[4]:239-48; Agnantis, N. J. et al [2003] "TUMOR MARKERS. AN UPDATE APPROACH FOR THEIR PROGNOSTIC SIGNIFICANCE. PART I. IN VIVO," 17[6]:609-18; Riley, R. D. et al. [2004] "A SYSTEMATIC REVIEW OF MOLECULAR AND BIOLOGICAL TUMOR MARKERS IN NEUROBLASTOMA," Clin Cancer Res. 10[1 Pt 1]:4-12; Given, M. et al. [2000] "THE PREDICTIVE OF TUMOUR MARKERS CA 15-3, TPS AND CEA IN BREAST CANCER RECURRENCE," Breast. 9[5]:277-80).

Currently available cancer markers measure cancer antigens. For example, prostate cancer can be diagnosed by measuring the prostate-specific antigen (PSA) cancer marker (Gretzer, M. B. et al. [2003] "PSA MARKERS IN PROSTATE CANCER DETECTION," Urol Clin North Am. 30[4]:677-86). The Carcino-Embryonic Antigen (CEA) marker has been found to have diagnostic utility in assessing colorectal cancer (Crawford, N. P. et al. [2003] "TUMOR MARKERS AND COLORECTAL CANCER: UTILITY IN MANAGEMENT," J Surg Oncol. 84[4]:239-48). The cancer antigen, CA15-3, has been correlated with breast cancer (Cheung, K. L. et al. [2003] "OBJECTIVE MEASUREMENT OF REMISSION AND PROGRESSION IN METASTATIC BREAST CANCER BY THE USE OF SERUM TUMOUR MARKERS," Minerva Chir. June; 58[3]:297-303). The cancer antigen, CA19-9, has been employed to diagnose gastrointestinal cancer (Grotowski, M. [2002] "ANTIGENS [CEA AND CA 19-9] IN DIAGNOSIS AND PROGNOSIS COLORECTAL CANCER," Pol Merkuriusz Lek. 12[67]:77-80; Trompetas, V. et al. [2002] "GIANT BENIGN TRUE CYST OF THE SPLEEN WITH HIGH SERUM LEVEL OF CA 19-9," Eur J Gastroenterol Hepatol. 14[1]:85-8). The cancer antigen, CA125, has been used to diagnose ovarian cancer (Anderiesz, C. et al [2003] "SCREENING FOR OVARIAN CANCER," Med J Aust. 178[12]:655-6).

The majority of solid tumors show chromosomal instability caused by aberrations in chromosomal segregation during cell division. Several enzymatic kinases are involved in maintaining proper chromosomal segregation and regulating cell cycle progression. One such kinase, cAMP-dependent protein kinase (PKA), appears to have a functional role in many aspects of cell signaling, metabolism, and proliferation (Matyakhina, L. et al. [2002] "PROTEIN KINASE A AND CHROMOSOMAL STABILITY," Ann NY Acad Sci. 968:148-57; Tortora, G. et al. [2002] "PROTEIN KINASE A AS TARGET FOR NOVEL INTEGRATED STRATEGIES OF CANCER THERAPY," Ann NY Acad Sci. 968:139-47).

Mammalian cells possess two types of cAMP-dependent protein kinase (PKA) species (Krebs, E. G. et al [1979] "PHOSPHORYLATION-DEPHOSPHORYLATION OF ENZYMES," Annu Rev Biochem. 48:923-39). These protein kinases are designated type I (PKA-I) and type II (PKA-II); they are distinguished by different regulatory subunits (R subunits) RI and RII, and share a common catalytic subunit (C subunit) (Beebe, S. J. et al. [1986] "CYCLIC NUCLEOTIDE-DEPENDENT PROTEIN KINASES," In: The Enzymes: Control by Phosphorylation, E. G. Krebs et al. [Eds] Academic Press: Orlando and London. pp. 43-11).

Traditionally, the enzyme activity of protein kinases has been assayed by following the transfer of a radioactive phosphate group from ($\gamma$-$^{32}$P) ATP to a residue of a suitable protein or peptide substrate (See, e.g., Witt, J. J. et al. [1975] Anal Biochem. 66:253-8; Casnellie, J. E. [1991] Methods Enzymol. 200:115-20; U.S. Pat. No. 6,498,005). PKA enzyme assays have been described (Cohen, C. B. et al. [1999] "A MICROCHIP-BASED ENZYME ASSAY FOR PROTEIN KINASE A," Anal Chem. [1999] 273:89-97; Cho, Y. S. et al [2000] "EXTRACELLULAR PROTEIN KINASE A AS A CANCER BIOMARKER: ITS EXPRESSION BY TUMOR CELLS AND REVERSAL BY A MYRISTATE-LACKING $C_{ALPHA}$ AND $RII_{BETA}$ SUBUNIT OVEREXPRESSION," Proc Natl Acad Sci USA. 97[2]:835-40).

Through biochemical studies and gene cloning, four isoforms of the R subunits, RI$\alpha$, RI$\beta$, RII$\alpha$, and RII$\beta$, have been identified (Amieux, P. S. et al [2002] "THE ESSENTIAL ROLE OF RI ALPHA IN THE MAINTENANCE OF REGULATED PKA ACTIVITY," Ann NY Acad Sci. 968:75-95; McKnight, G. S. et al. [1988] "ANALYSIS OF cAMP-DEPENDENT PROTEIN KINASE SYSTEM USING MOLECULAR GENETIC APPROACHES," Recent Prog Honn Res. 44:307-35; Levy, F. O. et al. [1988] "MOLECULAR CLONING, COMPLEMENTARY DEOXYRIBONUCLEIC ACID STRUCTURE AND PREDICTED FULL-LENGTH AMINO ACID SEQUENCE OF THE HORMONE-INDUCIBLE REGULATORY SUBUNIT OF 3',5'-CYCLIC ADENOSINE MONOPHOSPHATE-DEPENDENT PROTEIN KINASE FROM HUMAN TESTIS," Mol Endocrinol. 2:1364-73).

Importantly, the ratios of PKA-I to PKA-II can change dramatically during cell development, differentiation, and transformation (Lohmann, S. M. et al. [1984] "REGULATION OF THE CELLULAR AND SUBCELLULAR CONCENTRATIONS AND DISTRIBUTION OF CYCLIC NUCLEOTIDE-DEPENDENT PROTEIN KINASES," In:

Advances in Cyclic Nucleotide and Protein Phosphorylation Research, P. Greengard et al. [Eds] Raven Press: New York. pp. 63-117; Cho-Chung, Y. S. [1990] "ROLE OF CYCLIC AMP RECEPTOR PROTEINS IN GROWTH, DIFFERENTIATION, AND SUPPRESSION OF MALIGNANCY: NEW APPROACHES TO THERAPY," Cancer Res. 50:7093-100; Cho-Chung, Y. S. [2003] "cAMP SIGNALING IN CANCER GENESIS AND TREATMENT," Cancer Treat Res. 115: 123-43).

The cAMP signaling pathway has been proposed as a therapeutic target in lymphoid malignancies (Lerner, A. et al. [2000] "THE cAMP SIGNALING PATHWAY AS A THERAPEUTIC TARGET IN LYMPHOID MALIGNANCIES," Leuk Lymphoma. 37[1-2]: 39-51; Cho-Chung, Y. S. et al. [1995] "cAMP-DEPENDENT PROTEIN KINASE: ROLE IN NORMAL AND MALIGNANT GROWTH," Crit Rev Oncol Hematol. 21[1-3]:33-61; Cho-Chung, Y. S. et a. [1993] "THE REGULATORY SUBUNIT OF cAMP-DEPENDENT PROTEIN KINASE AS A TARGET FOR CHEMOTHERAPY OF CANCER AND OTHER CELLULAR DYSFUNCTIONAL-RELATED DISEASES," Pharmacol Ther. 60[2]:265-88). Increased expression of RIα/PKA-I has been shown in human cancer cell lines and primary tumors, as compared with normal counterparts (Cho-Chung, Y. S. [1990] "ROLE OF CYCLIC AMP RECEPTOR PROTEINS IN GROWTH, DIFFERENTIATION, AND SUPPRESSION OF MALIGNANCY: NEW APPROACHES TO THERAPY," Cancer Res. 50:7093-100; Miller, W. R. et al [1993] "TYPES OF CYCLIC AMP BINDING PROTEINS IN HUMAN BREAST CANCERS," Eur J Cancer. 29A:989-91) in cells after transformation with chemical or viral carcinogens and the Ki-ras oncogene or transforming growth factor-α, and on stimulation of cell growth with the granulocyte-macrophage colony-stimulating factor or phorbol esters (Cho-Chung, Y. S. [1990] "ROLE OF CYCLIC AMP RECEPTOR PROTEINS IN GROWTH, DIFFERENTIATION, AND SUPPRESSION OF MALIGNANCY: NEW APPROACHES TO THERAPY," Cancer Res. 50:7093-100; Cho-Chung, Y. S. et al. [2002] "DISSECTING THE CIRCUITRY OF PROTEIN KINASE A AND cAMP SIGNALING IN CANCER GENESIS: ANTISENSE, MICROARRAY, GENE OVEREXPRESSION, AND TRANSCRIPTION FACTOR DECOY," Ann NY Acad Sci. 968:22-36). Conversely, a decrease in the expression of RIα/PKA-I correlates with growth inhibition induced by site-selective cAMP analogs and antisense oligonucleotides targeted against the RIα subunit of PKA in a broad spectrum of human cancer cell lines and human tumors grown in nude mice (Cho-Chung, Y. S. et al. [1989] "SITE-SELECTIVE CYCLIC AMP ANALOGS AS NEW BIOLOGICAL TOOLS IN GROWTH CONTROL, DIFFERENTIATION AND PROTO-ONCOGENE REGULATION," Cancer Inv. 7:161-77; Cho-Chung, Y. S. et al [1999] "ANTISENSE DNA-TARGETING PROTEIN KINASE A-RIα SUBUNIT: A NOVEL APPROACH TO CANCER TREATMENT," Front Biosci. 4:D898-D907).

It has been previously demonstrated that various cancer cell types excrete PKA into the conditioned medium (Cho, Y. S. et al. [2000] "EXTRACELLULAR PROTEIN KINASE A AS A CANCER BIOMARKER: ITS EXPRESSION BY TUMOR CELLS AND REVERSAL BY A MYRISTATE-LACKING $C_{ALPHA}$ AND $RII_{BETA}$ SUBUNIT OVEREXPRESSION," Proc Natl Acad Sci USA. 97[2]:835-40). This extracellular protein kinase A (ECPKA) is present in active, free catalytic subunit (C subunit) form ("PKA Cα") and its activity is specifically inhibited by the PKA inhibitory protein PKI. Overexpression of the Cα or RIα subunit gene of PKA in an expression vector, which upregulates intracellular PKA-I, markedly upregulates ECPKA expression. In contrast, overexpression of the RII subunit—which eliminates PKA-I, upregulates PKA-II, and reverts the transformed phenotype—downregulates ECPKA. A mutation in the Cα gene that prevents myristylation allows intracellular PKA upregulation but blocks the ECPKA increase, suggesting that the $NH_2$-terminal myristyl group of Cα is required for ECPKA expression. In the serum of cancer patients, ECPKA expression is markedly upregulated, in contrast to normal serum (Cho, Y. S. et al. [2000]"EXTRACELLULAR PROTEIN KINASE A AS A CANCER BIOMARKER: ITS EXPRESSION BY TUMOR CELLS AND REVERSAL BY A MYRISTATE-LACKING $C_{ALPHA}$ AND $RII_{BETA}$ SUBUNIT OVEREXPRESSION," Proc Natl Acad Sci USA. 97[2]:835-40).

The development of monoclonal antibodies has led to the identification of numerous tumor-associated antigens in the serum and tissues of patients with malignancies. Protein products of oncogenes and tumor suppressor genes can be detected in extracellular fluids and serve as potential markers for carcinogenesis in vivo. Some of these growth factors are encoded by oncogenes. For example, higher levels of p21-ras protein are encoded by the ras oncogenes found in patients' blood. Circulating antibodies against p53 tumor suppressor protein have been found in sera of patients with breast and lung carcinomas and in children with B-lymphomas (Winter, S. F. et al. [1992] "DEVELOPMENT OF ANTIBODIES AGAINST P53 IN LUNG CANCER PATIENTS APPEARS TO BE DEPENDENT ON THE TYPE OF P53 MUTATION." Cancer Res. 52:4168-74; Lubin, R., et al. [1993] "ANALYSIS OF P53 ANTIBODIES IN PATIENTS WITH VARIOUS CANCERS DEFINE B-CELL EPITOPES OF HUMAN P53: DISTRIBUTION ON PRIMARY STRUCTURE AND EXPOSURE ON PROTEIN SURFACE." Cancer Res. 53:5872-6; Crawford, L. V., et al. [1982] "DETECTION OF ANTIBODIES AGAINST THE CELLULAR PROTEIN P53 IN SERA FROM PATIENTS WITH BREAST CANCER." Int. J. Cancer. 30:403-8). Antibodies against oncogenes such as c-myc and c-myb have also been found in sera of patients with colorectal and breast tumors (Sorokine, I., K. et al. [1991] "PRESENCE OF CIRCULATING ANTI-C-MYB ONCOGENE PRODUCT ANTIBODIES IN HUMAN SERA." Int. J. Cancer. 47:665-9; Ben-Mahrez, K., et al. [1988] "DETECTION OF CIRCULATING ANTIBODIES AGAINST C-MYC PROTEIN IN CANCER PATIENT SERA." Br J Cancer. 57:529-34; Ben-Mahrez, K., et al. [1990] "CIRCULATING ANTIBODIES AGAINST C-MYC ONCOGENE PRODUCT IN SERA OF COLORECTAL CANCER PATIENTS." Int J Cancer. 46:35-8).

In addition to the above-mentioned novel markers, some other proteins, hormones, and enzymes have been used as markers for the past 30 years. Notable among these are carcinoembryonic antigen (CEA), α-fetoprotein (AFP), human chorionic gonadotropin (HCG), and prostatic acid phosphatase (PAP). Most of these markers lack specificity, however. These levels are also increased under benign conditions and during gestation. All of these markers are based on the antigen determination method; the markers are lack of specificity and sensitivity. There is great need to discover novel biomarkers and translate them to routine clinical use. The present invention is directed to such need.

SUMMARY OF THE INVENTION

The present invention relates to a highly sensitive enzyme immunoassay (EIA) for measuring IgG antibody against extracellular protein kinase A (ECPKA). Sera from 295 patients with various types of cancer and 100 persons without cancer was tested. It was found that the frequency of anti-ECPKA IgG antibody was significantly higher in cancer patients (92%) than in those without (14%) cancer. There was no significant correlation between anti-ECPKA IgG antibody measured by EIA and ECPKA antigen measured by PKA enzymatic assay, and the anti-ECPKA IgG antibody-EIA method gave greater sensitivity and specificity than the ECPKA enzymatic assay. These results demonstrate that the approach of autoantibody analysis rather than conventional antigen analysis provides a useful approach for diagnosing cancer.

In detail, the invention provides an immunoassay that measures the presence or concentration of an anti-ECPKA autoantibody in a biological sample of a mammal, wherein the immunoassay comprises the steps of:

(a) contacting the biological sample with an antigen specific for an anti-ECPKA autoantibody, the contacting being under conditions sufficient to permit anti-ECPKA autoantibody if present in the sample to bind to the antigen and form an antigen-anti-ECPKA autoantibody complex;

(b) contacting the formed antigen-anti-ECPKA autoantibody complex with an anti-ECPKA autoantibody binding molecule, the contacting being under conditions sufficient to permit the anti-ECPKA autoantibody binding molecule to bind to anti-ECPKA autoantibody of the formed antigen-anti-ECPKA autoantibody complex and form an extended complex; and (c) determining the presence or concentration of the anti-ECPKA autoantibody in the biological sample by determining the presence or concentration of the formed extended complex.

The invention further concerns the embodiment of the above-described immunoassay wherein the antigen specific for an anti-ECPKA autoantibody is an extracellular PKA protein.

The invention further concerns the embodiments of the above-described immunoassays wherein in the anti-ECPKA autoantibody is an antibody of a mammalian species that differs from that of the mammal and is specific for antibodies produced by the mammal.

The invention further concerns the embodiments of the above-described immunoassays wherein the mammal is a human and the anti-ECPKA autoantibody is a human IgG antibody. The invention further concerns the embodiments of the above-described immunoassays wherein the anti-ECPKA autoantibody binding molecule is detectably labeled (especially with a chemical or enzyme label).

The invention further concerns the embodiments of the above-described immunoassays wherein in the step (a), the antigen specific for an anti-ECPKA autoantibody is immobilized to a solid support prior to the contacting with the biological sample.

The invention further concerns the embodiments of the above-described immunoassays wherein in the step (a), the antigen specific for an anti-ECPKA autoantibody is immobilized to a solid support subsequent to the contacting with the biological sample.

The invention further concerns the embodiments of the above-described immunoassays wherein the immunoassay is an immunochromatographic immunoassay, wherein:

in the step (a), the biological sample is placed in contact with a first porous carrier, the first porous carrier containing a non-immobilized, labeled antigen specific for an anti-ECPKA autoantibody;

in the step (b), the formed antigen-anti-ECPKA autoantibody complex is placed in contact with a second porous carrier, the second porous carrier being in communication with the first porous carrier, and containing an immobilized anti-ECPKA autoantibody binding molecule; and in the step (c), the presence or concentration of the anti-ECPKA autoantibody in the biological sample is determined by detecting the presence of the labeled antigen specific for an anti-ECPKA autoantibody in the second porous carrier.

The invention an immunological complex comprising an antigen specific for an anti-ECPKA autoantibody bound to an anti-ECPKA autoantibody, wherein the anti-ECPKA autoantibody is additionally bound to an anti-ECPKA autoantibody binding molecule.

The invention further concerns the embodiment of the above-described immunological complex wherein the antigen specific for an anti-ECPKA autoantibody is an extracellular PKA protein.

The invention further concerns the embodiments of the above-described immunological complexes wherein the anti-ECPKA autoantibody binding molecule is detectably labeled (especially with a chemical or enzyme label).

The invention further concerns the embodiments of the above-described immunological complexes wherein the anti-ECPKA autoantibody binding molecule is an immunological molecule. The invention further concerns the embodiments of the above-described immunological complexes wherein the anti-ECPKA autoantibody is a human autoantibody, and the anti-ECPKA auto antibody binding molecule is an anti-human IgG antibody.

The invention further concerns a kit for measuring the presence or concentration of an anti-ECPKA autoantibody in a biological sample of a mammal, wherein the kit comprises a hollow casing comprising a multilayer filter system, and first and second porous carriers, wherein the second porous carrier is in communication with the first porous carrier, and the first porous carrier is in communication with the multilayer filter system, a portion of which is accessible from the casing; wherein:

the first porous carrier contains a non-immobilized, labeled PKA C$\alpha$ or C$\alpha$ fragments; and the second porous carrier contains an immobilized, unlabeled antibody that binds to human IgG.

The invention further concerns the embodiment of the above-described kit wherein the labeled PKA C$\alpha$ is ECPKA (especially a chemical or enzyme label).

The invention further concerns the embodiments of the above-described kits wherein the kit detects human anti-ECPKA autoantibodies, and the antibody that binds to human IgG is an antibody of a nonhuman mammal.

DESCRIPTION OF THE PREFERRED EMBODIMENTS

The present invention relates to compositions and methods for the detection of anti-ECPKA autoantibodies in a biological sample, and to the use of such compositions and methods in the diagnosis of cancer in humans and non-human mammals (especially canine, feline, bovines, ovine, porcine, and equine mammals).

An extracellular form of PKA (ECPKA) is secreted from cancer cells (Cho, Y. S. et al. [2000] "EXTRACELLULAR PROTEIN KINASE A AS A CANCER BIOMARKER: ITS EXPRESSION BY TUMOR CELLS AND REVERSAL BY A MYRISTATE-LACKING $C_{ALPHA}$ AND $RII_{BETA}$ SUBUNIT OVEREXPRESSION," Proc Natl Acad Sci USA. 97[2]:835-40). The present invention derives in part from the recognition that ECPKA secretion elicits the formation of serum autoantibodies and that the presence and/or concentration of such autoantibodies can serve as a cancer diagnostic and prognostic marker. As described herein, the invention provides a highly sensitive immunoassay that measures the concentration and/or presence of anti-ECPKA autoantibody (especially an anti-ECPKA IgG antibody) in biological samples of suspected and confirmed cancer patients. This autoantibody-based immunoassay method provides a routine diagnostic procedure for detecting various cancer cell types.

The present invention concerns the binding of antigens and antibodies. As used herein, an "epitope" is a 2- or 3-dimensional region of an antigen that is recognized by and that specifically binds to an antibody. As used herein, an antigen and antibody are said to be "specific" for one another, or to "recognize" one another, or to "bind" to one another if they are capable of immunospecific binding to one another.

Any of a wide variety of assay formats may be used in accordance with the methods of the present invention. Such formats may be heterogeneous or homogeneous, sequential or simultaneous, competitive or noncompetitive. U.S. Pat. Nos. 5,563,036; 5,627,080; 5,633,141; 5,679,525; 5,691,147; 5,698,411; 5,747,352; 5,811,526; 5,851,778; and 5,976,822 illustrate several different assay formats and applications. Such assays can be formatted to be quantitative, to measure the concentration or amount of an anti-ECPKA autoantibody, or they may be formatted to be qualitative, to measure the presence or absence of an anti-ECPKA autoantibody.

Heterogeneous immunoassay techniques typically involve the use of a solid phase material to which the reaction product becomes bound, but may be adapted to involve the binding of nonimmobilized antigens and antibodies (i.e., a solution-phase immunoassay). The reaction product is separated from excess sample, assay reagents, and other substances by removing the solid phase from the reaction mixture (e.g., by washing). One type of solid phase immunoassay that may be used in accordance with the present invention is a sandwich immunoassay. In the sandwich assay, the more analyte present in the sample, the greater the amount of label present on the solid phase. This type of assay format is generally preferred, especially for the visualization of low analyte concentrations, because the appearance of label on the solid phase is more readily detected.

In accordance with a preferred embodiment of the present invention, antigen that is specifically reactive with an anti-ECPKA autoantibody is bound to a solid support (i.e., immobilized) and incubated in contact with the biological sample being tested for the presence of anti-ECPKA IgG antibody. As will be appreciated, the antigen may be incubated with the biological sample in an unbound state and then subsequently bound to the solid support (i.e., immobilizable). The supports are then preferably extensively treated (e.g., by washing, etc.) to substantially remove non-ECPKA IgG antibodies that may be present but which failed to bind to the bound antigen. In consequence of such treatment, an immune complex forms between the antigen and anti-ECPKA IgG antibody.

A detectably labeled second antibody (e.g., an anti-human IgG antibody) is then preferably added and the support is incubated under conditions sufficient to permit the second antibody to bind to any anti-ECPKA IgG antibody that may be present. The support is then preferably extensively treated (e.g., by washing, etc.) to substantially remove any unbound second antibody. If the anti-ECPKA IgG antibody is present in the test sample, then the two antibodies will form an immune complex with the analyte (i.e., a second antibody/anti-ECPKA IgG antibody/antigen sandwich). In such an assay, the detection of second antibody bound to the support is indicative of anti-ECPKA IgG antibody in the fluid being tested. Sandwich assay formats are described by Schuurs et al. U.S. Pat. Nos. 3,791,932 and 4,016,043, and by Pankratz, et al., U.S. Pat. No. 5,876,935. The second antibody may be a natural immunoglobulin isolated from nonhuman primates (e.g., anti-human IgG murine antibody, anti-human IgG goat antibody, etc.), or can be produced recombinantly or synthetically. It may be an intact immunoglobulin, or an immunoglobulin fragment (e.g., FAb, F[Ab]$_2$, etc.). As desired, other binding molecules (capable of binding to anti-ECPKA autoantibodies) may be employed in concert with or in lieu of such second antibodies. For example, the anti-ECPKA autoantibodies can be biotinylated and the second antibody can be replaced with labeled avidin or streptavidin.

To eliminate the bound-free separation step and reduce the time and equipment needed for a chemical binding assay, a homogeneous assay format may alternatively be employed. In such assays, one component of the binding pair may still be immobilized; however, the presence of the second component of the binding pair is detected without a bound-free separation. Examples of homogeneous optical methods are the EMIT method of Syva, Inc. (Sunnyvale, Calif.), which operates through detection of fluorescence quenching; the laser nephelometry latex particle agglutination method of Behringwerke (Marburg, Germany), which operates by detecting changes in light scatter; the LPIA latex particle agglutination method of Mitsubishi Chemical Industries (Tokyo, Japan); the TDX fluorescence depolarization method of Abbott Laboratories (Abbott Park, Ill.); and the fluorescence energy transfer method of Cis Bio International (Paris, France). Any of such assays may be adapted for use in accordance with the objectives of the present invention.

The binding assay of the present invention may be configured as a competitive assay. In a competitive assay, the more anti-ECPKA IgG antibody present in the test sample, the lower the amount of label present on the solid phase.

In a manner similar to the sandwich assay, the competitive assay can be conducted by providing a defined amount of a labeled anti-ECPKA IgG antibody and determining whether the fluid being tested contains anti-ECPKA IgG antibody that would compete with the labeled antibody for binding to the support. In such a competitive assay, the amount of captured labeled antibody is inversely proportional to the amount of analyte present in the test sample. Smith (U.S. Pat. No. 4,401,764) describes an alternative competitive assay format using a mixed binding complex that can bind analyte or labeled analyte but in which the analyte and labeled analyte cannot simultaneously bind the complex. Clagett (U.S. Pat. No. 4,746,631) describes an immunoassay method using a reaction chamber in which an analyte/ligand/marker conjugate is displaced from the reaction surface in the presence of test sample analyte and in which the displaced analyte/ligand/marker conjugate is immobilized at a second reaction site. The conjugate includes biotin, bovine serum albumin, and synthetic peptides as the ligand component of the conjugate, and enzymes, chemiluminescent materials, enzyme inhibitors, and radionucleotides as the marker component of the conjugate. Li (U.S. Pat. No. 4,661,444) describes a competitive immunoassay using a conjugate of an anti-idiotype antibody and a second antibody, specific for a detectable label, in which the detectable response is inversely related to the presence of analyte in the sample. Allen (European Patent Appln. No. 177,191) describes a binding assay involving a conjugate of a ligand analog and a second reagent, such as fluorescein, in which the conjugate competes with the analyte (ligand) in binding to a labeled binding partner specific for the ligand, and in which the resultant labeled conjugate is then separated from the reaction mixture by means of solid phase carrying a binding partner for the second reagent. This binding assay format combines the use of a competitive binding technique and a reverse sandwich assay configuration; i.e., the binding of conjugate to the labeled binding member prior to separating conjugate from the mixture by the binding of the conjugate to the solid phase. The assay result, however, is determined as in a conventional competitive assay in which the amount of label bound to the solid phase is inversely proportional to the amount of analyte in the test sample. Chieregatt et al. (GB Patent No. 2,084,317) describe a similar assay format using an indirectly labeled binding partner specific for the analyte. Mochida et al. (U.S. Pat. No. 4,185,084) also describe the use of a double-antigen conjugate that competes with an antigen analyte for binding to an immobilized antibody and that is then labeled. This method also results in the detection of label on a solid phase in which the amount of label is inversely proportional to the amount of analyte in the test sample. Sadeh et al. (U.S. Pat. No. 4,243,749) describe a similar enzyme immunoassay in which a hapten conjugate competes with analyte for binding to an antibody immobilized on a solid phase. Any of such variant assays may be used in accordance with the present invention.

In all such assay formats, at least one component of the assay reagents will preferably be labeled or otherwise detectable by the evolution or quenching of light. Such component may be a second antibody, anti-ECPKA IgG antibody, or an antigen that binds to an anti-ECPKA IgG antibody, depending on the immunoassay format employed. Radioisotopic-binding assay formats (e.g., a radioimmunoassay, etc.) employ a radioisotope as such label; the signal is detectable by the evolution of light in the presence of a fluorescent or fluorogenic moiety (see Lucas et al. [U.S. Pat. No. 5,698,411] and Landrum et al. [U.S. Pat. No. 5,976,822]). Enzymatic-binding assay formats (e.g., an ELISA, etc.) employ an enzyme as a label; the signal is detectable by the evolution of color or light in the presence of a chromogenic or fluorogenic moiety. Other labels, such as paramagnetic labels, materials used as colored particles, latex particles, colloidal metals such as selenium and gold, and dye particles (see U.S. Pat. Nos. 4,313,734; 4,373,932, and 5,501,985) may also be employed. The use of enzymes (especially alkaline phosphatase, $\beta$-galactosidase, horse radish peroxidase, or urease) as the detectable label (i.e., an enzyme immunoassay or EIA) is preferred.

The presence of enzymatic labels may be detected through the use of chromogenic substrates (including those that evolve or adsorb fluorescent, UV, visible light, etc.) in response to catalysis by the enzyme label. More preferably, chemical labels may be employed (e.g., colloidal gold, latex bead labels, etc.). Detection of label can be accomplished using multiple detectors, multipass filters, gratings, or spectrally distinct fluors (see e.g., U.S. Pat. No. 5,759,781), etc. It is particularly preferred to employ peroxidase as an enzyme label, especially in concert with the chromogenic substrate 3,3',5,5'-tetramethylbenzidine (TMB). In the case of labeling of the antibodies with peroxidase as enzyme, it is possible to use the periodate technique (Nakane, P. K. et al. [1974] "PEROXIDASE-LABELED ANTIBODY. A NEW METHOD OF CONJUGATION," J Histochem Cytochem. 22:1084-90) or a method reported in which the partners are linked with a heterobifunctional reagent (Ishikawa, E. et al. [1983] "ENZYME-LABELING OF ANTIBODIES AND THEIR FRAGMENTS FOR ENZYME IMMUNOASSAY AND IMMUNOHISTOCHEMICAL STAINING," J Immunoassay. 4[3]:209-327).

Any of a wide variety of solid supports may be employed in the immunoassays of the present invention. Suitable materials for the solid support are synthetics such as polystyrene, polyvinyl chloride, polyamide, or other synthetic polymers, natural polymers such as cellulose, as well as derivatized natural polymers such as cellulose acetate or nitrocellulose, and glass, especially glass fibers. The support can take the form of spheres, rods, tubes, and microassay or microtiter plates. Sheet-like structures such as paper strips, small plates, and membranes are likewise suitable. The surface of the carriers can be permeable and impermeable for aqueous solutions.

Although the foregoing description pertains to assaying for the presence of anti-ECPKA autoantibodies in biological samples that are fluids (e.g., sera, blood, urine, saliva, pancreatic juice, cerebrospinal fluid, semen, etc.), it will be appreciated that any fluidic biological sample (e.g., tissue or biopsy extracts, extracts of feces, sputum, etc.) may likewise be employed in the assays of the present invention. Most preferably, the biological sample being assayed will be serum.

Materials for use in the assay of the invention are ideally suited for the preparation of a kit. Such a kit may comprise a carrier means being compartmentalized to receive in close confinement; one or more containers means vials, tubes and the like; each of the containers means comprising one of the separate elements to be used in the method. For example, one of the containers means may comprise a suitable antigen (such as ECPKA (PKA C$\alpha$, or C$\alpha$ fragments) or an extract of one or more different types of cancer cells and tumors) bound to a solid support. A second container may comprise soluble, detectably labeled second antibody, preferably in lyophilized form, or in solution. In addition, the kit may also contain one or more containers, each of which comprises a (different) predetermined amount of ECPKA (PKA C$\alpha$, or C$\alpha$ fragments) or anti-ECPKA (PKA C$\alpha$) autoantibody. These latter containers can be used to prepare a standard curve into which can be interpolated the results obtained from the sample containing the unknown amount of autoantibodies to ECPKA.

In using the kit, all the user has to do is add to a container a premeasured amount of a sample suspected of containing a measurable yet unknown amount of autoantibodies to ECPKA, a premeasured amount of support-bound antigen present in the first container, and a premeasured amount of the detectably labeled second antibody present in the second container. After an appropriate time for incubation, an immune complex is formed and is separated from the supernatant fluid, and the immune complex or the supernatant fluid are detected, as by radioactive counting, addition of an enzyme substrate, and color development, or by inclusion of a chemical label (e.g., colloidal gold, latex beads, etc.).

The present invention particularly relates to the use of immunochromatographic assay formats to detect anti-ECPKA autoantibodies. In a preferred immunochromatographic assay format, two contacting, but spatially distinct, porous carriers are employed. The first such carrier will contain a non-immobilized, labeled PKA Cα or Cα fragments (e.g., ECPKA [Cα] or protease digests or Cα) and the second such carrier will contain an immobilized, but unlabeled antibody that binds to IgG (e.g., where human anti-ECPKA autoantibodies are being assayed, the unlabeled antibody may be an anti-human IgG antibody).

Preferably, the device will comprise a hollow casing constructed of, for example, a plastic material, etc., in which the first carrier will communicate indirectly with the interior of the casing via a multilayer filter system that is accessible from the device (e.g., by protruding therefrom or by being incompletely covered by the device), such that a serum, plasma, or whole blood test sample can be applied directly to the filter system and will permeate therefrom into the first porous carrier. In such a device, the permeation of fluid containing anti-ECPKA autoantibodies will cause the non-immobilized labeled PKA Cα or Cα fragments of the first carrier to become bound to the migrating antibodies, and will then permeate into the second carrier. Because the second carrier contains immobilized antibody that binds human IgG, any labeled PKA Cα or Cα fragments entering the second carrier will be entrapped therein.

Detection of labeled PKA Cα or Cα fragments in the carrier containing the immobilized unlabeled antibody thus indicates that anti-ECPKA autoantibodies are present in the sample being evaluated. The assay can be made quantitative by measuring the quantity of labeled PKA Cα or Cα fragments that become bound within the second porous carrier.

Having now generally described the invention, the same will be more readily understood through reference to the following examples, which are provided by way of illustration and are not intended to be limiting of the present invention, unless specified.

Example 1

Comparative Evaluation of Anti-ECPKA Autoantibody Immunoassay and PKA Enzymatic Assay in Diagnosing Cancer in Humans Materials and Methods Subjects: Serum samples are taken from 295 human patients with various cancer cell types and from 100 persons without cancer.

Enzyme-linked immunoabsorbent assay (ELISA): Anti-ECPKA IgG autoantibody in the sera of cancer patients and healthy individuals are measured by solid-phase ELISA assay. For such assays, round-bottom polyvinyl chloride microtiter plates (Thermolab System, Helsinki, Finland) are coated with 100 µl of diluted (50 µg per ml concentration with PBS) purified recombinant human PKA Cα antigen (see Purification of PKA Cα, Materials and Methods). The plates are incubated at room temperature for 1 hour, then washed one time with washing buffer (20 mM Hepes, 0.9% NaCl, 30 mM sucrose-0.1% bovine serum albumin [BSA], pH 7.0), and each well is blocked for 2 hours at room temperature with 100 µl of Blockace (Serotec, http://www.serotec.com) dissolved in water (4 g/400 ml), then the plates are washed two times with Na citrate washing solution (50 mM Na citrate, 0.15 M NaCl, 0.1% polyoxyethylenesorbitan monolaurate Tween® 20, pH 5.0-5.2). The serum samples are diluted to 25,000-fold with sample dilution buffer (PBS pH 7.4, 0.25% BSA [fatty acid free fraction V], 0.05% Tween 20), and 100 µl of diluted samples are added to each well, then incubated for 1 hour at 37° C. After three washes with the Na citrate washing solution, 100 µl of 20,000-fold diluted anti-human IgG-HRP antibody-enzyme conjugate (Jackson ImmunoResearch Laboratories, West Grove, Pa.) in PBS, 1% BSA is added to the wells, after which the plates are incubated for 1 hour at room temperature. After washing the plates five times in Na citrate washing solution, 100 µl of TMB substrate is added. The reaction is stopped with 100 µl of 0.45 M $H_2SO_4$ reagent, after which the absorbance at 450 nm is recorded on an ELISA reader (BioRad [Hercules, Calif.] microplate reader benchmark). ELISA specificity is confirmed by performing the inhibition test simultaneously on serum samples that have been incubated for 1 hr at room temperature with the above antigen at a final concentration of 1 mg/mL.

Purification of PKA Cα: The recombinant human PKA Cα (1.1 kb) from OT1529-Cα plasmid (Cho, Y. S. et al. [2000] "EXTRACELLULAR PROTEIN KINASE A AS A CANCER BIOMARKER: ITS EXPRESSION BY TUMOR CELLS AND REVERSAL BY A MYRISTATE-LACKING $C_{ALPHA}$ AND $RII_{BETA}$ SUBUNIT OVEREXPRESSION," Proc Natl Acad Sci USA. 97[2]:835-40) is infused with pQE31 DNA leading to production of pQE-Cα (Hong, S. H. Seoul National University, Seoul, Korea, unpublished). pQE-Cα plasmid was expressed in *E coli* and purification of native PKA Cα protein was achieved (Paragon, Baltimore, Md.).

PKA Assays: The enzyme activity of PKA is measured by the method of Rohlff, C. et al. (1993) ("8-Cl-cAMP INDUCES TRUNCATION AND DOWN-REGULATION OF THE RI ALPHA SUBUNIT AND UP-REGULATION OF THE RII BETA SUBUNIT OF CAMP-DEPENDENT PROTEIN KINASE LEADING TO TYPE II HOLOENZYME-DEPENDENT GROWTH INHIBITION AND DIFFERENTIATION OF HL-60 LEUKEMIA CELLS," J Biol Chem. 268:5774-82). For the measurement of serum ECPKA activity, the assay (total volume, 50 µl) is carried out for 20 min at 37° C. in the reaction mixture (containing 50 mM Tris HCl [pH 7.5], 1 mM DTT, 10 mM $MgCl_2$, 5 µM Kemptide [a synthetic substrate for PKA; GIBCO/BRL], 1.2 µM [γ-$^{32}$P]ATP [25 Ci/mmol; ICN] with or without 5 µM cAMP and 5 µM PKI), and 10 µl of serum. After incubation, the reaction mixtures are spotted onto phosphocellulose disks (GIBCO/BRL) and washed three times in 0.5% phosphoric acid. Filters are air dried and counted by liquid scintillation counter. One unit of PKA activity is defined as the amount of enzyme that transferred 1 pmol of $^{32}$P from (γ-$^{32}$P)ATP to recovered protein in 1 min at 37° C. in the standard assay system. LDH activity is measured by the use of a commercial kit (Sigma).

Results

The sera of human patients and normal control individuals is tested using the above-described ELISA, expressing anti- ECPKA autoantibody titers arbitrarily as ratios to the mean absorbance of the normal control sera. From anti-ECPKA autoantibody titers of normal controls, a ratio greater than 1.0 is considered positive.

Figure 1:
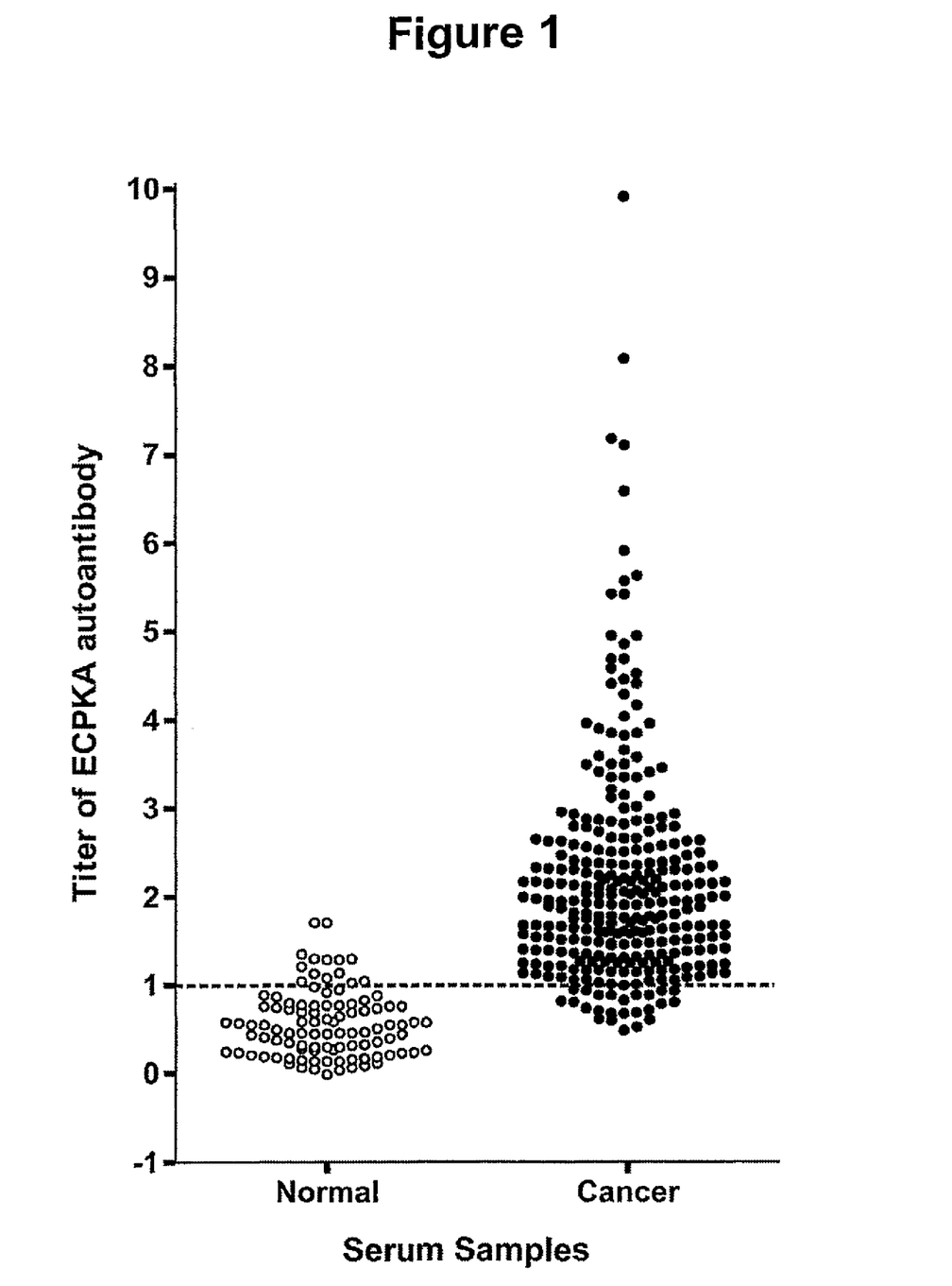
FIG. 1 shows values obtained using a preferred immunoassay format of the present invention with normal individuals and cancer patients. Both frequency and mean titer of the patients are significantly higher (frequency=92%, mean titer 2.2) than those of the normal controls (frequency 14%, mean titer 0.6). Values greater than 1.0 (above the dashed line) are positive.

The assay is found to be reproducible, with within-run and between-run CVs of <8.8% and <9.0%, respectively. Values for anti-ECPKA autoantibody in sera from cancer patients are shown in FIG. 1. Both frequency and mean titer of the patients are significantly higher (frequency=92%, mean titer 2.2) than those of the normal controls (frequency 14%, mean titer 0.60).

Figure 2:
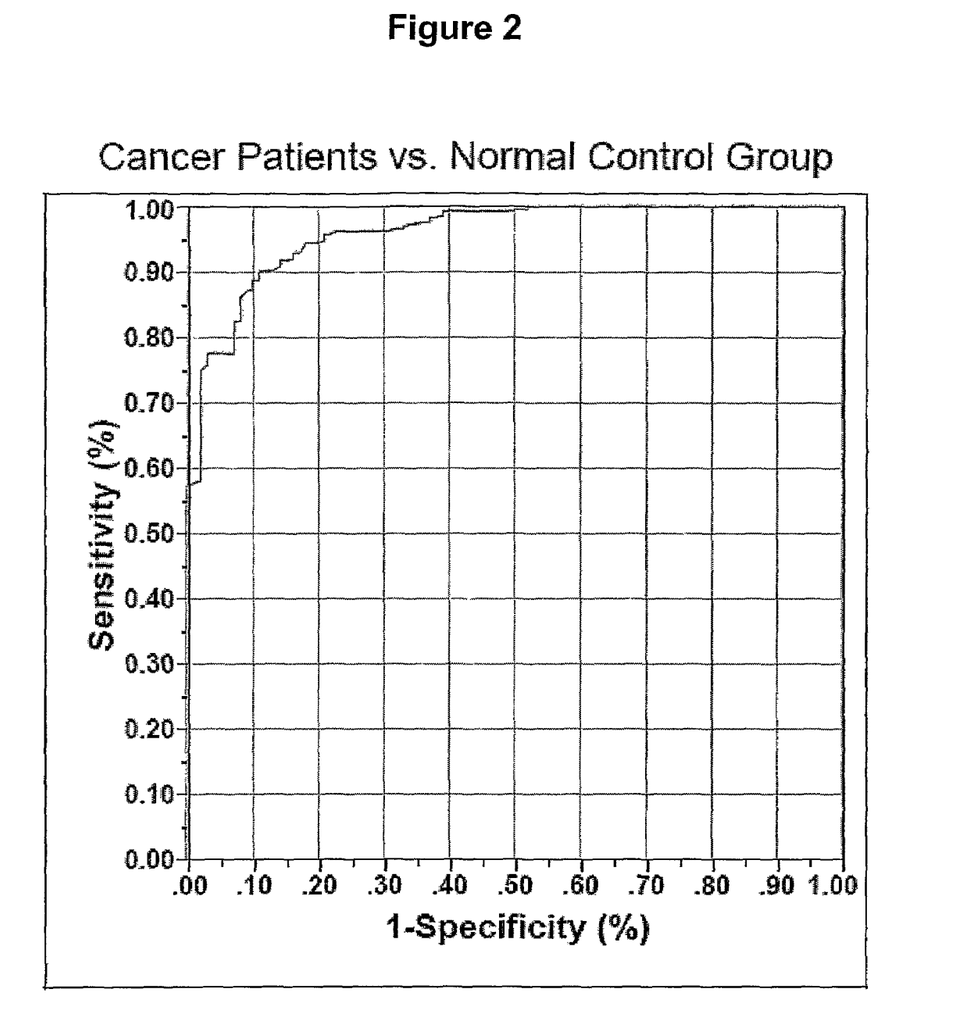
FIG. 2 shows a receiver operating characteristic (ROC) curve of an anti-ECPKA autoantibody ELISA (FIG. 1). At the point of intersection, the cutoff value for the ELISA assay is 1.0 titer, and the sensitivity and specificity are 90% and 89%, respectively.

The sensitivity and specificity of the ELISA assay calculated at different cut-off values are graphically presented in a receiver operating characteristic (ROC) curve (FIG. 2). At the point of interaction, the cut-off value for anti-ECPKA autoantibody titer is 1.0 (FIG. 1) and the sensitivity and specificity for the ELISA test are 90% and 89%, respectively.

Figure 3:
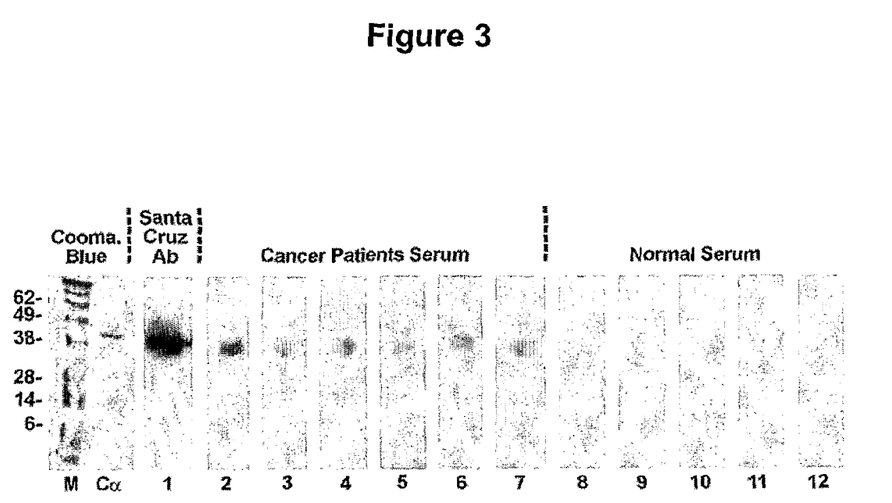
FIG. 3 shows the results of a Western blotting analysis of anti-ECPKA autoantibody in cancer patients' serum. The lanes containing M (mw marker) and C$\alpha$ (1 µg) are stained with Coomassie Blue; strip 1 was blotted with Santa Cruz Ab anti-C$\alpha$ antibody (Santa Cruz Biotechnology, Santa Cruz, Calif.); strips 2-7 were blotted with cancer patients' serum (10,000-fold dilution); strips 8-12 were blotted with normal person serum (10,000-fold dilution); strips 1-12 contained purified PKA C$\alpha$ (2 µg each).

Immunoblotting identified anti-ECPKA autoantibody in cancer patients' serum (FIG. 3). Randomly selected patients sera exhibited immunocross-reactivity toward the purified PKA C$\alpha$ protein (40 kDa) (FIG. 3, strips 2-7), while no such immunocross-reactivity for C$\alpha$ protein was observed in normal serum (FIG. 3, strips 8-12).

Figure 4:
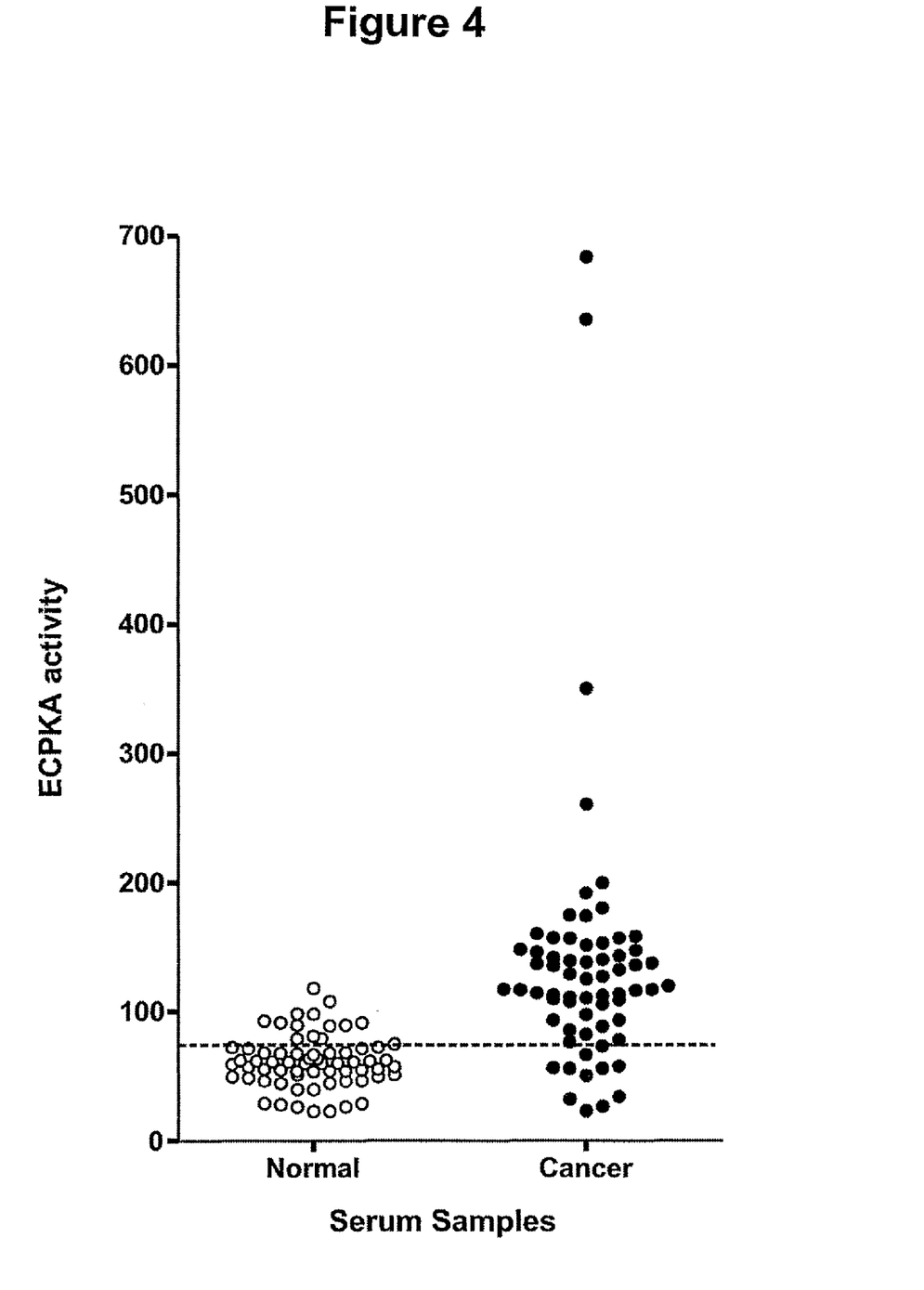
FIG. 4 shows values obtained using an ECPKA enzymatic assay as a control of the sensitivity and discriminatory ability of the immunoassay formats of the present invention. Values obtained from normal individuals and cancer patients are shown (cancer patients, frequency=83%, mean value=130 mU/ml; normal individual controls, frequency=21%, mean value=60 mU/ml) indicating a lack of sensitivity and specificity. Values greater than 75 mU/ml (above the dashed line) are positive.

The ECPKA enzymatic assay (which measures antigen concentration) gives a significant overlap between cancer patients (n=66) and normal controls (n=66) in frequency and mean values (patients, frequency=83%, mean value=130 mU/ml; normal controls, frequency=21%, mean value=60 mU/ml) indicating a lack of sensitivity and specificity (FIG. 4).

Figure 5:
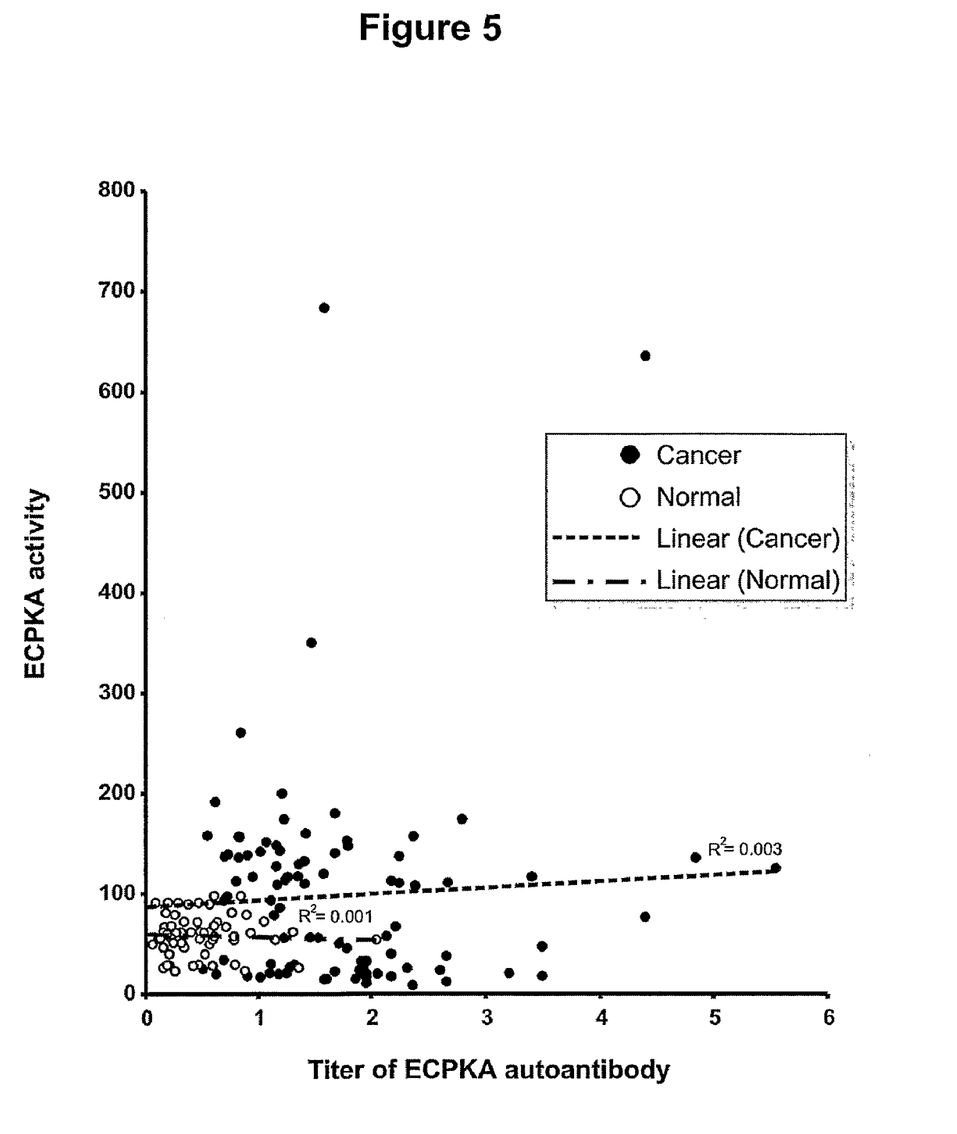
FIG. 5 shows the results of a correlation study between anti-ECPKA antibody titer and ECPKA enzymatic activity in sera from cancer patients and healthy persons. Coefficients of 0.003 for cancer patients and 0.001 for healthy persons are statistically insignificant.

A comparison of individual anti-ECPKA autoantibody titers obtained by ELISA and ECPKA measured by PKA enzymatic assay is shown in FIG. 5. There is no correlation between the titers of anti-ECPKA IgG antibody obtained by ELISA and ECPKA measured by enzymatic assay (ECPKA antigen measurement).

Example 2

Conclusions Regarding Anti-ECPKA Autoantibody Immunoassay and its Use in Cancer in Humans The present invention demonstrates that the sera presence of autoantibody directed against ECPKA is highly correlative of cancer. The ELISA developed for anti-ECPKA autoantibody is highly sensitive and specific, exhibiting markedly high anti-ECPKA autoantibody titers (mean titer 2.2, frequency 92%) in cancer patients, but exhibits low or negative titers and frequency (14%) in normal individual controls. A comparison of the frequency detected by ELISA with that detected by enzymatic assay shows that the ELISA that detects the autoantibody for ECPKA is highly sensitive and specific compared with the enzymatic assay that measures antigen activity.

Figure 6:
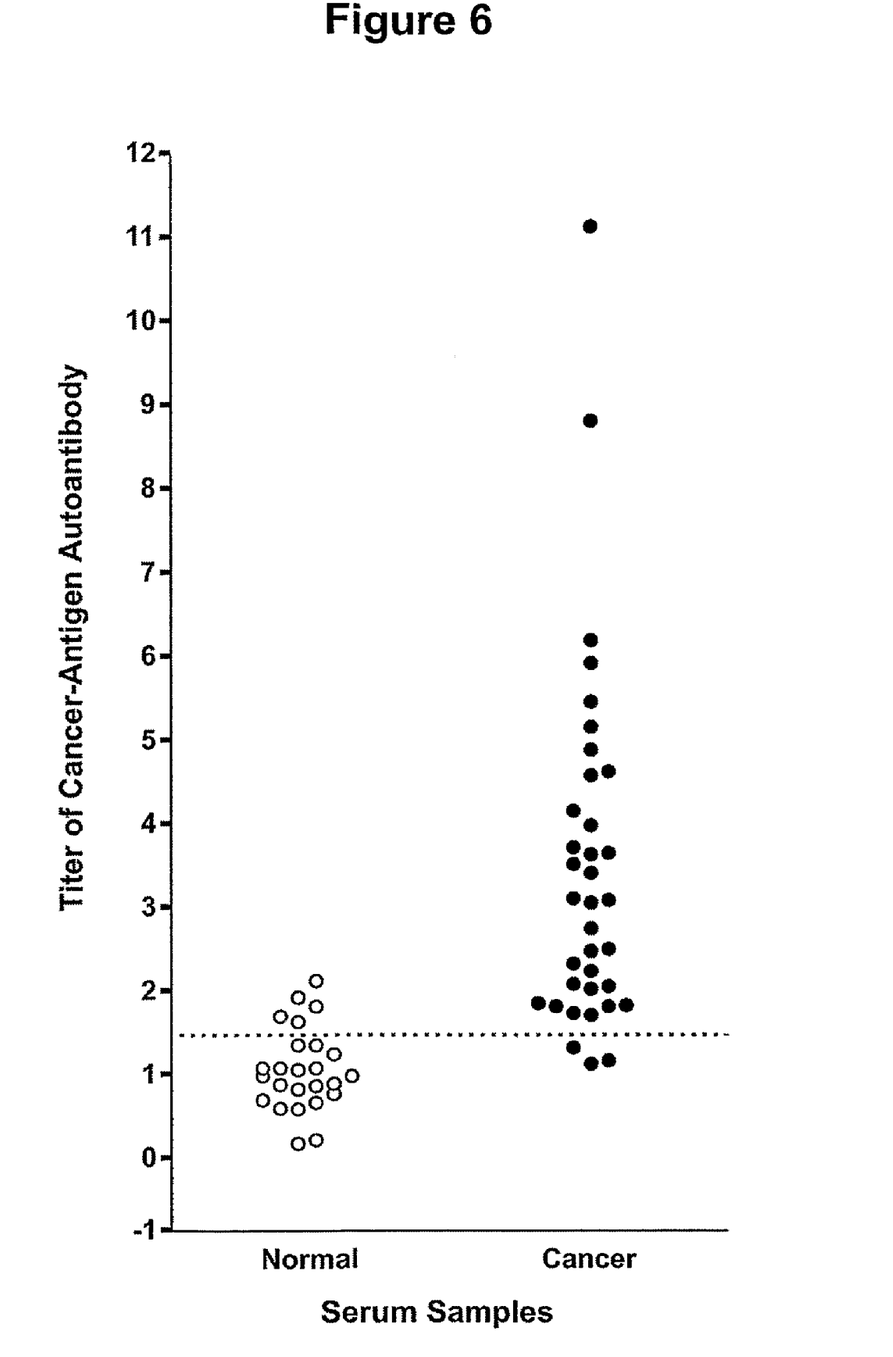
FIG. 6 shows the titer of anticancer antigen antibodies in sera from cancer patients and healthy persons using HCT-15 tumor extracts as a source of cancer antigens. Values>1.5 (broken line) are positive.
Figure 7:
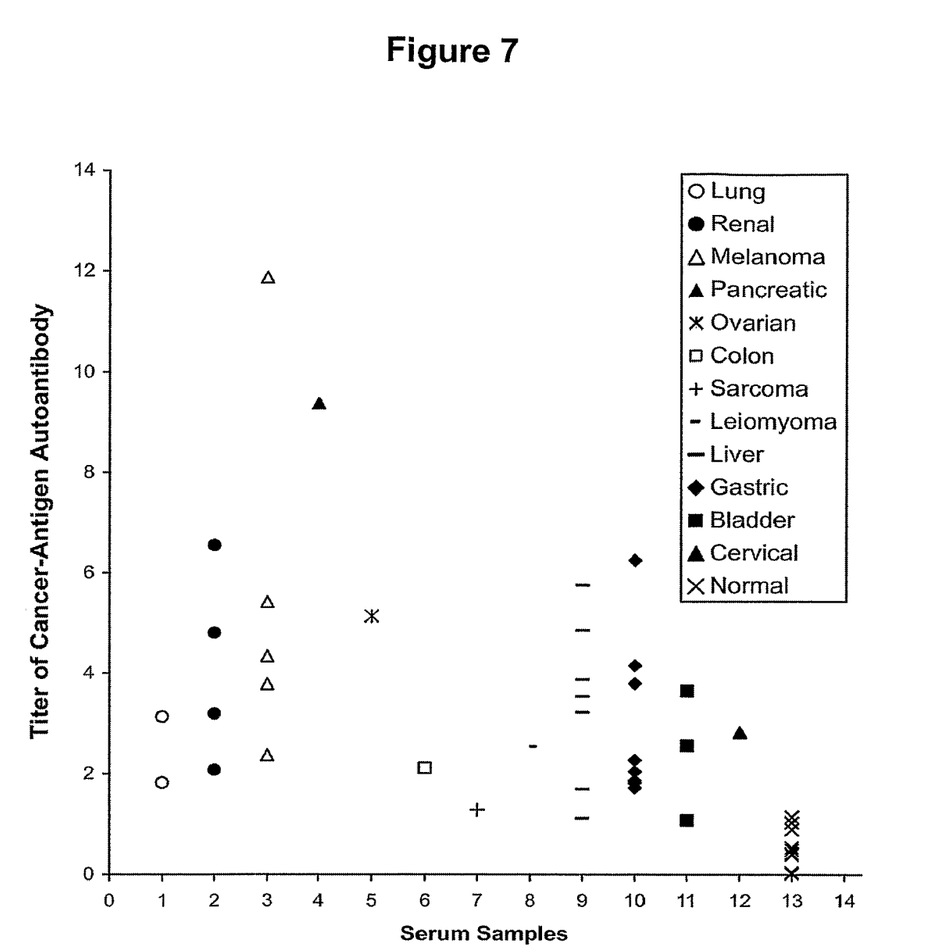
FIG. 7 shows the observed titers of antigen antibodies in sera from cancer patients with different types of cancers (lung, renal, pancreatic, ovarian, colon, liver, gastric, bladder, and cervical carcinomas, melanoma, sarcoma, and leiomyoma).

To examine whether the autoantibody detection method of the present invention can be extended to other cancer antigens (extracellular secreted), the following experiment is performed: HCT-15 tumor (a multidrug-resistant human colon carcinoma grown in nude mice) is used as a cancer antigen source. The tumor is homogenized in Buffer #10 (20 mM Tris-HCl pH 7.4, 100 mM NaCl, 0.5% sodium deoxycholate, 5 mM MgCl$_2$, protease inhibitor cocktail set 1 [Calbiochem]) (1:3), 1 part tumor (weight), 3 parts buffer (volume). The homogenate is centrifuged for 10 min at 10,000 rpm and the supernatant is collected (Extract). The Extract is incubated with protein-A sepharose (3:1), rotating 1 hr, 4° C., and the preparation is centrifuged for 2 min at 6,000 rpm. The supernatant is collected and dialyzed against PBS overnight at 4° C. After such dialysis, the extract is ready to use for coating microtiter plates in an ELISA. FIG. 6 shows the titer of anticancer antigen antibodies in sera from cancer patients (n=36) and healthy persons (n=25). Values>1.5 (broken line) are positive. FIG. 7 shows the observed titers of antigen antibodies in sera from cancer patients with different types of cancer (lung, renal, melanoma, pancreatic, ovarian, colon, liver, gastric, bladder, and cervical carcinomas, and sarcoma and leiomyoma. The patients' sera (n=36) and normal sera (n=25) are the same as those of FIG. 6.

The results demonstrate that it is possible to use the autoantibody detection method of the present invention to detect cancer antigens in humans and animals. The results indicate that ELISA for detecting autoantibodies rather than antigens for ECPKA and other cancer antigens provides a new approach for diagnosing cancer in humans and animals.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An immunoassay that measures the presence or concentration of an anti-ECPKA autoantibody in a biological sample of a mammal, wherein said immunoassay comprises the steps of: (a) contacting said biological sample with an antigen specific for an anti-ECPKA autoantibody, said contacting being under conditions sufficient to permit anti-ECPKA autoantibody if present in said sample to bind to said antigen and form an antigen-anti-ECPKA autoantibody complex; (b) contacting said formed antigen-anti-ECPKA autoantibody complex with an anti-ECPKA autoantibody binding molecule, said contacting being under conditions sufficient to permit said anti-ECPKA autoantibody binding molecule to bind to anti-ECPKA autoantibody of said formed antigen-anti-ECPKA autoantibody complex and form an extended complex; and (c) determining the presence or concentration of said anti-ECPKA autoantibody in said biological sample by determining the presence or concentration of said formed extended complex.

2. The immunoassay of claim 1, wherein said antigen specific for an anti-ECPKA autoantibody is an extracellular PKA protein.

3. The immunoassay of claim 1, wherein in said anti-ECPKA autoantibody is an antibody of a mammalian species that differs from that of said mammal and is specific for antibodies produced by said mammal.

4. The immunoassay of claim 3, wherein said mammal is a human and said anti-ECPKA autoantibody is a human IgG antibody.

5. The immunoassay of claim 1, wherein said anti-ECPKA autoantibody binding molecule is detectably labeled.

6. The immunoassay of claim 5, wherein said detectable label is a chemical label.

7. The immunoassay of claim 1, wherein in said step (a), said antigen specific for an anti-ECPKA autoantibody is immobilized to a solid support prior to said contacting with said biological sample.

8. The immunoassay of claim 1, wherein in said step (a), said antigen specific for an anti-ECPKA autoantibody is immobilized to a solid support subsequent to said contacting with said biological sample.

9. The immunoassay of claim 1, wherein said immunoassay is an immunochromatographic immunoassay, wherein: in said step (a), said biological sample is placed in contact with a first porous carrier, said first porous carrier containing a non-immobilized, labeled antigen specific for an anti-ECPKA autoantibody; in said step (b), said formed antigen-anti-ECPKA autoantibody complex is placed in contact with a second porous carrier, said second porous carrier being in communication with said first porous carrier, and containing an immobilized anti-ECPKA autoantibody binding molecule; and in said step (c), the presence or concentration of said anti-ECPKA autoantibody in said biological sample is determined by detecting the presence of said labeled antigen specific for an anti-ECPKA autoantibody in said second porous carrier.

10. An isolated immunological complex comprising an antigen specific for an anti-ECPKA autoantibody bound to an anti-ECPKA autoantibody, wherein said anti-ECPKA autoantibody is additionally bound to an anti-ECPKA autoantibody binding molecule.

11. The immunological complex of claim 10, wherein said antigen specific for an anti-ECPKA autoantibody is an extracellular PKA protein.

12. The immunological complex of claim 10, wherein said anti-ECPKA autoantibody binding molecule is detectably labeled.

13. The immunological complex of claim 12, wherein detectable label is a chemical label.

14. The immunological complex of claim 10, wherein said anti-ECPKA autoantibody binding molecule is an immunological molecule.

15. The immunological complex of claim 14, wherein said anti-ECPKA autoantibody is a human autoantibody, and said anti-ECPKA autoantibody binding molecule is an anti-human IgG antibody.

16. A kit for measuring the presence or concentration of an anti-ECPKA autoantibody in a biological sample of a mammal, wherein said kit comprises a hollow casing comprising a multilayer filter system, and first and second porous carriers, wherein said second porous carrier is in communication with said first porous carrier, and said first porous carrier is in communication with said multilayer filter system, a portion of which is accessible from said casing; wherein: said first porous carrier contains a non-immobilized, labeled PKA Cα or Cα fragments; and said second porous carrier contains an immobilized, unlabeled antibody that binds to human IgG.

17. The kit of claim 16, wherein said labeled PKA Cα is ECPKA.

18. The kit of claim 16, wherein said label of said labeled PKA Cα is a chemical label.

19. The kit of claim 16, wherein said kit detects human anti-ECPKA autoantibodies, and said antibody that binds to human IgG is an antibody of a nonhuman mammal.

20. An immunological complex comprising an antigen specific for an anti-ECPKA autoantibody bound to an anti-ECPKA autoantibody, wherein said anti-ECPKA autoantibody is additionally bound to an anti-ECPKA autoantibody binding molecule; and wherein at least one of the antigen or the anti-ECPKA autoantibody binding molecule is labeled or bound to a solid support.

* * * * *